(12) United States Patent
Matani et al.

(10) Patent No.: US 9,018,266 B2
(45) Date of Patent: Apr. 28, 2015

(54) DEFOAMER FOR FERMENTATION

(75) Inventors: Satoko Matani, Kawasaki (JP); Susumu Tanaka, Kawasaki (JP)

(73) Assignee: NOF Corporation, Tokyo (JP)

( * ) Notice: Subject to any disclaimer, the term of this patent is extended or adjusted under 35 U.S.C. 154(b) by 0 days.

(21) Appl. No.: 14/008,226

(22) PCT Filed: Mar. 28, 2012

(86) PCT No.: PCT/JP2012/058071
§ 371 (c)(1),
(2), (4) Date: Sep. 27, 2013

(87) PCT Pub. No.: WO2012/133491
PCT Pub. Date: Oct. 4, 2012

(65) Prior Publication Data
US 2014/0194538 A1    Jul. 10, 2014

(30) Foreign Application Priority Data
Mar. 30, 2011    (JP) ................................. 2011-074936

(51) Int. Cl.
*B01D 19/04* (2006.01)
*C12N 1/20* (2006.01)
*C12N 1/00* (2006.01)

(52) U.S. Cl.
CPC .............. *B01D 19/0404* (2013.01); *C12N 1/20* (2013.01); *Y10S 435/812* (2013.01)

(58) Field of Classification Search
CPC ....... B01D 19/04; B01D 19/0404; C12N 1/20
USPC ................ 516/134, 133; 435/266, 301.1, 812
See application file for complete search history.

(56) References Cited

U.S. PATENT DOCUMENTS

| 2,470,808 | A | * | 5/1949 | Keiser et al. ................... 516/189 |
| 5,120,397 | A | * | 6/1992 | Urushibata et al. ............ 510/174 |
| 5,282,928 | A | * | 2/1994 | Takahashi et al. ............ 510/174 |
| 5,567,606 | A | * | 10/1996 | Hayashi et al. ................ 516/133 |
| 5,843,734 | A |   | 12/1998 | Shonaka et al. |
| 5,994,415 | A | * | 11/1999 | Gruning et al. ................ 516/116 |
| 6,057,375 | A | * | 5/2000 | Wollenweber et al. ........ 516/133 |
| 2014/0194538 | A1 | * | 7/2014 | Matani et al. ................. 516/134 |

FOREIGN PATENT DOCUMENTS

| JP | 5-228308 A | 9/1993 |
| JP | 6-54680 A | 3/1994 |
| JP | 10-15305 A | 1/1998 |
| JP | 2001-178446 A | 7/2001 |
| WO | 97/00942 A1 | 1/1997 |

OTHER PUBLICATIONS

Machine Translation of Publ. No. JP 2001-178446, published Jul. 2001, Japan patent Office, Tokyo, Japan, obtained online @ http://dossier1.ipdl.inpit.go.jp/AIPN/odse_top_dn.ipdl?N0000=7400, pp. 1-7.*
Machine Translation of Publ. No. JP 05-228308, published Sep. 1993, Japan patent Office, Tokyo, Japan, obtained online @ http://dossier1.ipdl.inpit.go.jp/AIPN/odse_top_dn.ipdl?N0000=7400, pp. 1-10.*
Machine Translation of Publ. No. JP 10-015305, published Jan. 1998, Japan patent Office, Tokyo, Japan, obtained online @ http://dossier1.ipdl.inpit.go.jp/AIPN/odse_top_dn.ipdl?N0000=7400, pp. 1-7.*
Machine Translation of Publ. No. JP 2012205567, published Oct. 2012, Japan patent Office, Tokyo, Japan, obtained online @ http://dossier1.ipdl.inpit.go.jp/AIPN/odse_top_dn.ipdl?N0000=7400, pp. 1-12.*
International Search Report dated Jul. 3, 2012 issued in International Application No. PCT/JP2012/058071 (PCT/ISA/210).
Writen Opinion dated Jul. 3, 2012 issued in International Application No. PCT/JP2012/058071 (PCT/ISA/237).
Search Report dated Jul. 24, 2014, issued by the European Patent Office in counterpart European Application No. 12764088.6.

* cited by examiner

*Primary Examiner* — Daniel S Metzmaier
(74) *Attorney, Agent, or Firm* — Sughrue Mion, PLLC

(57) ABSTRACT

Provided is a defoamer for fermentation which has excellent dispersibility in water and forms neither a precipitate nor oil droplets when the dispersion is heated, and which is highly effective in defoaming fermentation media. This defoamer contains a reaction product obtained by mixing a fat or oil having an iodine value of 40 to 130 with glycerin or like in a molar ratio of from 3/2 to 1/2 to obtain a mixture, causing 4 to 17 mol of propylene oxide to add to 1 mol of the mixture, and then causing 20 to 40 mol of ethylene oxide and 70 to 110 mol of propylene oxide to block-wise add thereto in this order, the reaction product having an ethylene oxide/propylene oxide molar ratio of from 1/4 to 2/5.

1 Claim, No Drawings

DEFOAMER FOR FERMENTATION

TECHNICAL FIELD

The present invention relates to a defoamer for fermentation, i.e., to a fermentation defoamer which gives aqueous dilutions having excellent high-temperature stability and an excellent defoaming effect.

BACKGROUND ART

In the technology of fermentation, bubbles generate in large quantities especially in fermentation that requires stirring and aeration, and this foaming has conventionally posed problems concerning operations. In case where the gas-phase part of the fermenter is filled with bubbles, not only the volume efficiency of the fermenter decreases but also there is a possibility that the bubbles might overflow the tank to wet the lines outside the tank, resulting in contamination. In order to inhibit such decreases in operation efficiency due to foaming, defoamers are added to fermentation systems. Since fermentation is always accompanied with stirring and aeration, the performances required of defoamers for fermentation include: foam-breaking properties which enable the defoamers to come to break the foam from the moment of addition thereof; foam-inhibiting properties which continuously inhibit foaming; and no inhibitory effect on the ferment organism. As such defoamers, defoamers of the type obtained by causing an alkylene oxide to add to both a fat or oil and a polyhydric alcohol as starting materials have been in general use because these defoamers have little inhibitory effect on the ferment organism and show excellent foam-breaking properties and foam-inhibiting properties.

Fermentation defoamers are diluted beforehand and are thereby added to fermentation systems as a dilution which is an aqueous solution or suspension having an even concentration. A general fermentation apparatus is configured so that when the bubbles generated in the fermenter reach a given height, this state is detected by a sensor and a defoamer dilution is supplied from a storage tank and added to the fermenter via an automatic dropping device. Since fermentation defoamers must show the effect thereof at 30 to 40° C., which are fermentation temperatures, many of the defoamers have a cloud point at temperatures lower by 10 to 20° C. than those temperatures. Such a defoamer is difficult to dissolve in or mingle with water at temperatures not lower than the cloud point, and a dilution thereof is hence prepared by cooling the system to or below the cloud point and stirring the cooled system. Consequently, dispersibility in water at the optimum temperature is required.

The defoamer dilution is sterilized by heating in order to prevent microorganisms from coming into the fermentation vessel, and is thereafter cooled to around the fermentation temperature and then added to the fermentation vessel. Because of this, the defoamer is exposed to temperatures not lower than the cloud point as a result of the heating in the sterilization step and has reduced solubility in water. This defoamer hence tends to precipitate in a lower-layer part or form oil droplets in an upper-layer to middle-layer part.

With respect to the fermentation defoamers which have formed a precipitate or oil droplets upon thermal sterilization, among conventional fermentation defoamers of the alkylene oxide adduct type, the defoamer dilutions have a reduced defoamer concentration in the liquid portion because the precipitate or oil droplets do not disappear even when the temperature thereof is lowered from the sterilization temperature to the fermentation temperature. Consequently, even when a defoamer dilution in this state is added to the fermenter, the inherent defoaming effect is not obtained. A step is therefore necessary in which the defoamer dilution is cooled again to or below the cloud point and stirred to thereby make the dilution return to the homogeneous dilution. The steps become complicated.

For example, the fermentation defoamer described in patent document 1 (Japanese Laid-Open Patent Application: JP-A-5-228308) is a defoamer obtained by causing alkylene oxides to add to a mixture of a fat or oil and a polyhydric alcohol. However, the amount of the ethylene oxide which has added to the starting materials is small as compared with the amount of the propylene oxide which has added to the starting materials and, hence, dilutions of this defoamer disadvantageously form oil droplets when heated. Meanwhile, the defoamer described in patent document 2 (International Publication WO 97/00942) is a blend system which is a blend of a defoamer of the type described above with a higher fatty acid, higher alcohol, or the like, and continuously shows the effect thereof over a long period without affecting the fermentation results. However, the higher fatty acid or higher alcohol, as a component of the blend, considerably decreases in solubility when dilutions of the defoamer are heated. This defoamer hence forms a precipitate or oil droplets, resulting in a decrease in defoaming effect.

In contrast, the defoamer described in patent document 3 (Japanese Laid-Open Patent Application: JP-A-6-54680) has the same basic structure as the defoamers of the type described above. However, the amount of the ethylene oxide which has added, relative to the amount of the propylene oxide which has added, is large. Because of this, this defoamer is less apt to form a precipitate or oil droplets during thermal sterilization, but is insufficient in defoaming effect. The defoamer described in patent document 4 (Japanese Laid-Open Patent Application: JP-A-2001-178446) is a defoamer obtained by causing 1 to 10 mol of propylene oxide to add to a mixture of a fat or oil and a polyhydric alcohol and then causing ethylene oxide and propylene oxide to randomly add thereto. This defoamer is less apt to form a precipitate or oil droplets during thermal sterilization, but shows low foam-breaking properties just after addition thereof. Consequently, some time is required for the effect thereof to be produced.

There has hence been no known fermentation defoamer which combines excellent dispersibility in water and a high defoaming effect.

PRIOR-ART DOCUMENTS

Patent Documents

Patent Document 1: Japanese Laid-Open Patent Application: JP-A-5-228308
Patent Document 2: International Publication WO 97/00942
Patent Document 3: Japanese Laid-Open Patent Application: JP-A-6-54680
Patent Document 4: Japanese Laid-Open Patent Application: JP-A-2001-178446

SUMMARY OF THE INVENTION

Problems that the Invention is to Solve

A subject for the invention is to provide, in view of the problems described above, a defoamer for fermentation which shows excellent dispersibility in water in the preparation of a defoamer dilution therefrom and forms neither a precipitate nor oil droplets in the defoamer dilution in a thermal sterilization step and which is highly effective in defoaming fermentation media when the dilution is added thereto.

Means for Solving the Problems

The present inventors diligently made investigations in order to overcome the problems. As a result, the inventors have found that a fermentation defoamer having high dispersibility in water and excellent defoaming properties is obtained by causing propylene oxide to add, in a specific proportion, to a mixture of a fat or oil with glycerin or a propylene oxide adduct of glycerin (the number of moles of propylene oxide which had added, 1 to 4 mol) and subsequently causing ethylene oxide and propylene oxide to block-wise add thereto in this order. The invention has been thus completed.

Effects of the Invention

When the fermentation defoamer of the invention is used, the dilution thereof does not suffer precipitation through a thermal sterilization step and, by lowering the temperature thereof to a fermentation temperature and adding this dilution as such to the fermenter, the foaming can be inhibited rapidly and continuously. Consequently, the fermentation product is produced in an increased amount per unit fermenter and the yield thereof is improved.

Modes for Carrying out the Invention

The fat or oil to be used in the invention is a fat or oil which has an iodine value of 40 to 130. Iodine value is determined by a test method for reference fat analysis (2.3.4.1-1996; Wijs method). Examples of this fat or oil include sunflower oil, corn oil, cottonseed oil, sesame oil, rapeseed oil, rice oil, peanut oil, and olive oil. Especially preferred are palm oil and beef tallow. In case where the fat or oil has an iodine value lower than 40, a sufficient defoaming effect is not obtained. In case where the fat or oil has an iodine value exceeding 130, the ferment microorganism gives reduced fermentation results. From these standpoints, it is more preferred that the iodine value of the fat or oil should be 70 or less.

The propylene oxide adducts of glycerin which are usable in the invention are adducts obtained by causing 1 to 4 mol of propylene oxide to add to glycerin. In case where propylene oxide is caused to add in an amount exceeding 4 mol, a sufficient defoaming effect is not obtained.

In the invention, a fat or oil is mixed with one or more compounds selected from the group consisting of glycerin and propylene oxide adducts of glycerin. The ratio in which a fat or oil is mixed with one or more compounds selected from the group consisting of glycerin and propylene oxide adducts of glycerin (when two compounds are used, the sum thereof) is from 3/2 to 1/2 in terms of molar ratio ([fat or oil]/[one or more compounds selected from the group consisting of glycerin and propylene oxide adducts of glycerin]). In case where the molar ratio thereof exceeds 3/2, this mixture has too high a degree of esterification and reduced reactivity with the alkylene oxides and, hence, the reaction step requires much time. Consequently, this mixture is unsuitable for industrial production. In addition, when the reaction product obtained therefrom is diluted and heated, the reaction product is apt to form oil droplets or a precipitate, resulting in a decrease in defoaming effect. In case where the molar ratio thereof is less than 1/2, this mixture has a reduced degree of esterification and, hence, the reaction product not only shows impaired dispersibility in water when an aqueous solution and suspension thereof are prepared but also has a lessened defoaming effect. From the standpoint of the present invention, the molar ratio ([fat or oil]/[one or more compounds selected from the group consisting of glycerin and propylene oxide adducts of glycerin]) is more preferably 1/1 or less, and is preferably 4/7 or larger, more preferably 2/3 or larger, even more preferably 9/11 or larger.

Examples of the alkylene oxides to be used in the invention include ethylene oxide and propylene oxide. First, propylene oxide is caused to add to the mixture of a fat or oil with glycerin or a propylene oxide adduct (1 to 4 mol) of glycerin, the amount of the former propylene oxide being 4 to 17 mol (L mol) per mol of the whole mixture. In case where L is less than 4, a precipitate or oil droplets are formed through thermal sterilization. In case where L exceeds 17, a quick-defoaming effect is not obtained. From this standpoint, L is preferably 6 mol or larger, more preferably 10 mol or larger. Meanwhile, L is preferably 15 mol or less, more preferably 14 mol or less.

Subsequently, ethylene oxide is caused to add in an amount of 20 to 40 mol (M mol). In case where M is less than 20 mol, the resultant reaction product has reduced hydrophilicity and, hence, forms a precipitate through the step of thermally sterilizing the dilution thereof. In case where M exceeds 40 mol, a decrease in defoaming effect results. From the standpoint of the invention, the number of moles of ethylene oxide which is caused to add, M, is preferably 25 mol or larger, more preferably 30 mol or larger. Meanwhile, M is preferably 38 mol or less, more preferably 35 mol or less.

Furthermore, propylene oxide is caused to add in an amount of 70 to 110 mol (N mol). In case where N is less than 70 mol, a decrease in defoaming effect results. In case where N exceeds 110 mol, the reaction product has an increased viscosity and hence reduced dispersibility in water. From the standpoint of the invention, N is preferably 75 mol or larger, more preferably 80 mol or larger. Meanwhile, N is preferably 100 mol or less, more preferably 95 mol or less.

It is preferred that the mode of addition of the ethylene oxide and propylene oxide should be block-wise addition. In case where random addition is conducted, the resultant defoamer shows reduced foam-breaking properties just after addition thereof.

M/(L+N) is from 1/5 to 1/2. In case where M/(L+N) is less than 1/5, the resultant defoamer has heightened hydrophobicity and forms a precipitate or oil droplets after the sterilization. In case where M/(L+N) exceeds 1/2, a sufficient defoaming effect is not obtained. From this standpoint, M/(L+N) is preferably 1/4 or larger, more preferably 5/16 or larger. Meanwhile, M/(L+N) is preferably 2/5 or less, more preferably 30/83 or less.

With respect to the numbers of moles of PO which has added, it is preferred that L/N should be from 2/35 to 2/5. By regulating L/N to 2/35 or larger, the persistence of defoaming effect is improved. By regulating L/N to 2/5 or less, a quick-defoaming effect is obtained. From this standpoint, L/N is more preferably from 3/50 to 17/70, most preferably from 7/76 to 12/85.

It is preferred that L+M+N should be 94 to 167. By regulating L+M+N to 94 or larger, the defoaming effect is improved. By regulating L+M+N to 167 or less, the defoamer is made to have reduced viscosity and show improved dispersibility when a dilution thereof is prepared. From these standpoints, L+M+N is more preferably 110 to 150, most preferably 120 to 145.

When the defoamer of the invention is produced, a suitable reaction temperature is 80 to 160° C. The catalyst to be used may be any of the alkaline substances, the hydroxides or carbonates of alkali metals, and the like which are usually in use in those reactions. Examples thereof include sodium methylate, sodium hydroxide, potassium hydroxide, potassium carbonate, sodium acetate, and t-potassium butoxide. These catalysts may be directly introduced or may be introduced after being diluted with water. From the standpoint of enhancing the reactivity of the alkylene oxides, it is preferred to use the catalyst in an amount of about 0.01 to 0.5% by mass based on the reaction product. With respect to pressure during the reactions, it is more preferred to conduct the reactions at an elevated pressure of 1 MPa or less. After the reactions, a synthetic adsorbent having the property of adsorbing alkalis is added to and mixed with the reaction mixture and this mixture is filtered, in order to remove the catalyst. The catalyst may be neutralized with an organic or inorganic salt, e.g., acetic acid, phosphoric acid, or hydrochloric acid, or with an adsorbent, and the resultant mixture as such can be used as a product or can be used as a product after being filtered or after being dehydrated and then filtered.

The defoamer of the invention is diluted with water and dispersed or emulsified therein, and this defoamer dilution is subjected to a thermal sterilization step and then added (as a fermentation defoamer) to a fermenter.

The fermentation defoamer of the invention can be applied to fermentation for producing various substances. For example, this defoamer is usable in the fermentation of amino acids. Specific examples of the amino acid fermentation include fermentation of glutamic acid, aspartic acid, lysine, threonine, tryptophan, alanine, glycine, and the like.

It is preferred that the defoamer of the invention should be used in such a manner that the defoamer is added before initiation of incubation or during incubation in an amount of 0.0001 to 1% by mass, especially 0.0005 to 0.5% by mass, based on the culture medium. The incubation to which the fermentation defoamer of the invention is applied has an optimum temperature of 30 to 40° C., and examples thereof include aeration, stirring, or shaking incubation and the like, which undergo considerable foaming.

EXAMPLES (1) Synthesis of Defoamers

Example 1

Into a 5-L autoclave equipped with a stirrer, temperature sensor, and pressure gauge were introduced 169.6 g (0.2 mol) of palm oil and 18.4 g (0.2 mol) of glycerin. Thereto was added 9 g of potassium hydroxide as a catalyst. After the atmosphere in the system was replaced with nitrogen gas, the contents were heated to 110° C. and dehydrated for 2 hours at a reduced pressure of 0.04 MPa or less while bubbling nitrogen thereinto. Thereafter, 278.4 g (4.8 mol) of propylene oxide was gradually forced into the autoclave at 120° C. and a pressure of 0.6 MPa or less, and this mixture was thereafter continuously reacted under these conditions for 1 hour. Subsequently, 545.6 g (12.4 mol) of ethylene oxide was gradually forced into the autoclave, and the resultant mixture was continuously reacted under those conditions for 1 hour. Furthermore, 1,972 g (34 mol) of propylene oxide was forced into the autoclave, and this mixture was continuously reacted under those conditions for 2 hours. After completion of the reaction, the unreacted alkylene oxides were removed while passing nitrogen, and the potassium hydroxide as a catalyst was deactivated using hydrochloric acid. The resultant mixture was dehydrated and then filtered to thereby obtain 2,745.3 g (yield, 92%) of a defoamer of the invention.

(2) Examples 2 to 4 and Comparative Examples 1 to 5

Using the starting materials shown in Table 1, defoamers 2 to 4 of the invention and defoamers of Comparative Examples were obtained in the same manner as in Example 1.

In Table 1, "(EO)/(PO)" indicates random addition, and "(EO)-(PO)" indicates block addition.

[Dispersibility Test]

In a 100-mL measuring cylinder was introduced 99 mL of ion-exchanged water. One gram of a defoamer was added thereto. Thereafter, a stirrer chip ($\phi$5 mm×20 mm) was put thereinto, and the contents began to be stirred at a speed of 1,000 rpm. The time period from the initiation of stirring to even dissolution or suspension was measured, and this time period was evaluated in Table 2 as an index to dispersibility. All steps of the dispersibility test were conducted at room temperature.

[High-Temperature Stability Test]

Into a 100-mL lidded sample bottle were introduced 95 g of ion-exchanged water and 5 g of a defoamer sample. The contents were stirred until an even dilution was obtained. Thereafter, this dilution was thermally sterilized with an autoclave high-temperature pressure sterilizer (120° C., 2 kPa, 20 min) and was examined for appearance immediately thereafter. Furthermore, the sterilized dilution was thereafter cooled to 25° C. and then examined again for appearance. The results thereof are shown in Table 2.

TABLE 1

| | Sample No. | Raw-material fat or oil | Iodine value | Glycerin or propylene oxide adduct of glycerin | Molar ratio of starting materials | | Mode of EO/PO addition and number of moles of EO/PO which added per mole of the sum of fat or oil and either glycerin or propylene oxide adduct of glycerin | Molar ratio of EO/PO which added |
|---|---|---|---|---|---|---|---|---|
| | | | | | Fat or oil | Glycerin or propylene oxide adduct of glycerin | | |
| Products of the invention | 1 | palm | 52 | glycerin | 1 | 1 | $(PO)_{12}$-$(EO)_{31}$-$(PO)_{85}$ | 31/97 |
| | 2 | beef tallow | 53 | glycerin | 2 | 3 | $(PO)_7$-$(EO)_{30}$-$(PO)_{76}$ | 30/83 |
| | 3 | palm | 52 | propylene oxide (3 mol) adduct of glycerin | 1 | 1 | $(PO)_{10}$-$(EO)_{31}$-$(PO)_{85}$ | 31/95 |
| | 4 | palm | 52 | propylene oxide (3 mol) adduct of | 1 | 1 | $(PO)_{11}$-$(EO)_{34}$-$(PO)_{94}$ | 34/105 |

TABLE 1-continued

| | Sample No. | Raw-material fat or oil | Iodine value | Glycerin or propylene oxide adduct of glycerin | Molar ratio of starting materials | | Mode of EO/PO addition and number of moles of EO/PO which added per mole of the sum of fat or oil and either glycerin or propylene oxide adduct of glycerin | Molar ratio of EO/PO which added |
|---|---|---|---|---|---|---|---|---|
| | | | | | Fat or oil | Glycerin or propylene oxide adduct of glycerin | | |
| Comparative Example | 1 | beef tallow | 53 | glycerin | 2 | 3 | $(PO)_{10}$-[$(EO)_{20}$/$(PO)_{80}$] | 2/9 |
| | 2 | coconut | 9 | glycerin | 5 | 1 | $(PO)_{120}$-$(EO)_{36}$ | 1/4 |
| | 3 | palm kernel oil | 18 | glycerin | 3 | 2 | $(EO)_{15}$-$(PO)_{50}$ | 3/10 |
| | 4 | coconut | 9 | glycerin | 1 | 1 | $(PO)_{60}$-$(EO)_{45}$-$(PO)_{30}$ | 1/2 |
| | 5 | palm | 52 | glycerin | 63 | 37 | $(EO)_{31}$-$(PO)_{97}$ | 31/97 |

TABLE 2

| | Sample No. | Dispersibility (note 1) | High-temperature stability test (note 2) | |
|---|---|---|---|---|
| | | | just after sterilization | after cooling |
| Products of the invention | 1 | ○ | ○ | ○ |
| | 2 | ○ | ○ | ○ |
| | 3 | ○ | ○ | ○ |
| | 4 | ○ | ○ | ○ |
| Comparative products | 1 | ○ | ○ | ○ |
| | 2 | x | x | x |
| | 3 | ○ | Δ | x |
| | 4 | ○ | ○ | ○ |
| | 5 | ○ | Δ | x |

(Note 1)
○: becomes an even aqueous solution or suspension in 1 minute.
Δ: becomes an aqueous solution or suspension after lapse of 1 to 3 minutes.
x: does not disperse evenly.
(Note 2)
○: even aqueous solution or suspension
Δ: uneven suspension
x: aqueous solution or suspension in which a precipitate or oil droplets have been formed As apparent from Table 2, the fermentation defoamers of Examples 1 to 4 of the invention give stable dilutions as compared with some of the conventional defoamers. Meanwhile, defoamers for which a starting-material fat or oil was incorporated in a high proportion and which have a long alkylene oxide chain, like Comparative Example 2, not only are difficult to disperse in water at ordinary temperature but also form oil droplets through the sterilization step; it is impossible to redissolve the oil droplets. Defoamers in which the ethylene oxide content is far lower than the propylene oxide content, like Comparative Example 3, are apt to form oil droplets. Comparative Example 5 forms oil droplets when the dilution thereof is thermally sterilized and, hence, becomes insufficient in defoaming effect.

[Evaluation of Defoaming Property]

Into a 1,000-mL measuring cylinder was introduced 200 mL of a culture medium. A defoamer which had been diluted and thermally sterilized by the method shown in [High-Temperature Stability Test] was stirred with a stirrer chip (φ5 mm×20 mm) at a speed of 1,000 rpm and then sampled, and this sample was diluted 50 times with ion-exchanged water. The resultant defoamer dilution was added in an amount of 1 or 2 mL to the culture medium so that the system to be evaluated had a defoamer concentration of 0.0005 to 0.001%. Air was bubbled into the measuring cylinder held at a constant temperature of 38° C., through a diffusion stone at an air flow rate of 1,000 mL/min, and the height (mL) of the bubbles was measured after 10 minutes. The results thereof are shown in Table 3.

Incidentally, the samples in which oil droplets or a precipitate had been observed in the [High-Temperature Stability Test] were excluded from this test.

| Composition of Culture Medium | |
|---|---|
| Polypeptone | 1.0% by mass |
| Blackstrap molasses | 5.0% by mass |
| Urea | 0.1% by mass |
| $KH_2PO_4$ | 0.1% by mass |
| $MgSO_4 \cdot 7H_2O$ | 0.05% by mass |
| Water | remainder |
| Total weight | 100.0% by mass |

[Test for Examining Foam-Breaking Property]

Into a 10-mL lidded test tube was introduced 4 mL of liquid A, which contained a defoamer. This test tube was shaken at 38° C. for 5 minutes. One milliliter of liquid B was introduced thereinto, and the time period required for the bubbles to disappear was measured. The results thereof are shown in Table 3.

| Composition of Liquid A | |
|---|---|
| Polypeptone | 5.0% by mass |
| Sodium hydrogen carbonate | 10.0% by mass |
| Defoamer | 0.001% by mass |
| Water | remainder |
| Total weight | 100.0% by mass |

| Composition of Liquid B | |
|---|---|
| Polypeptone | 5.0% by mass |
| Citric acid | 10.0% by mass |
| Defoamer | 0.001% by mass |
| Water | remainder |
| Total weight | 100.0% by mass |

TABLE 3

|  | Sample No. | Evaluation of defoaming property (mL) | | Foam-breaking property (sec) |
| --- | --- | --- | --- | --- |
|  |  | 5 ppm | 10 ppm |  |
| Products of the invention | 1 | 60 | 30 | 24 |
|  | 2 | 80 | 50 | 28 |
|  | 3 | 70 | 40 | 26 |
|  | 4 | 60 | 40 | 25 |
| Comparative products | 4 | 220 | 140 | 200 |
|  | 7 | 250 | 140 | 180 |

As apparent from Table 3, the fermentation defoamers of Examples 1 to 4 of the invention have sufficient defoaming performance as compared with the conventional defoamers. Meanwhile, Comparative Example 1 lacks in quick-acting properties because the alkylene oxide chain is one formed by random polymerization, and does not show a sufficient defoaming effect because the proportion of the number of moles of ethylene oxide which added is low. Comparative Example 4 is insufficient in defoaming effect although having satisfactory dispersibility in water. In addition, this comparative defoamer does not show a quick-defoaming effect because the amount of the propylene oxide which underwent the first stage addition reaction was large.

While the invention has been described in detail and with reference to specific embodiments thereof, it will be apparent to one skilled in the art that various changes and modifications can be made therein without departing from the spirit and scope thereof.

This application is based on a Japanese patent application filed on Mar. 30, 2011 (Application No. 2011-74936), the entire contents thereof being incorporated herein by reference. All references cited herein are incorporated as a whole.

The invention claimed is:

1. A defoamer for fermentation comprising a reaction product obtained by
    (1) mixing a fat or oil having an iodine value of 40 to 130 with one or more compounds selected from the group consisting of glycerin and propylene oxide adducts of glycerin, to obtain a mixture, wherein said propylene oxide adducts of glycerin are obtained by adding 1 to 4 mol of propylene oxide to glycerin, wherein the molar ratio of said fat or oil/glycerin or propylene oxide adducts of glycerin is from 3/2 to 1/2 to obtain a mixture,
    (2) adding 4 to 17 mol of propylene oxide per 1 mol of the mixture, and
    (3) then adding 20 to 40 mol of ethylene oxide and 70 to 110 mol of propylene oxide by block-wise addition thereto in this order,
wherein the reaction product has an ethylene oxide/propylene oxide molar ratio of from 1/4 to 2/5.

* * * * *